United States Patent
Hucklenbroich et al.

(10) Patent No.: US 10,081,806 B2
(45) Date of Patent: Sep. 25, 2018

(54) RECOVERY OF A BIOMOLECULE COMPRISING AQUEOUS PHASE FROM A MULTIPHASIC MIXTURE

(71) Applicant: QIAGEN GMBH, Hilden (DE)

(72) Inventors: Jörg Hucklenbroich, Wermelskirchen (DE); Frank Narz, Witten (DE)

(73) Assignee: Qiagen GmbH, Hilden (DE)

( * ) Notice: Subject to any disclaimer, the term of this patent is extended or adjusted under 35 U.S.C. 154(b) by 408 days.

(21) Appl. No.: 14/357,958

(22) PCT Filed: Dec. 4, 2012

(86) PCT No.: PCT/EP2012/004987
§ 371 (c)(1),
(2) Date: May 13, 2014

(87) PCT Pub. No.: WO2013/083260
PCT Pub. Date: Jun. 13, 2013

(65) Prior Publication Data
US 2015/0004675 A1 Jan. 1, 2015

(30) Foreign Application Priority Data
Dec. 6, 2011 (EP) .................................... 11009631

(51) Int. Cl.
*C12M 1/00* (2006.01)
*C12N 15/10* (2006.01)
*C12Q 1/6806* (2018.01)

(52) U.S. Cl.
CPC ....... *C12N 15/1017* (2013.01); *C12N 15/101* (2013.01); *C12N 15/1003* (2013.01); *C12N 15/1006* (2013.01); *C12Q 1/6806* (2013.01)

(58) Field of Classification Search
USPC .......... 435/6.1, 6.11, 7.1, 91.1, 183; 436/94; 536/23.1; 530/300, 350
See application file for complete search history.

(56) References Cited

U.S. PATENT DOCUMENTS

| | | | |
|---|---|---|---|
| 4,236,515 A * | 12/1980 | Genese | A61M 5/1408 137/113 |
| 5,158,681 A | 10/1992 | Freeman et al. | |
| 6,464,880 B1 * | 10/2002 | Datta | B01D 61/02 156/43 |

FOREIGN PATENT DOCUMENTS

| | | |
|---|---|---|
| DE | 4300438 C1 | 6/1994 |
| EP | 1626085 A1 | 2/2006 |
| EP | 2395082 A1 | 12/2011 |
| WO | 94/15702 A1 | 7/1994 |
| WO | 02/46463 A2 | 6/2002 |
| WO | 2004/080579 A2 | 9/2004 |
| WO | 2005/010204 A2 | 2/2005 |
| WO | 2006/130632 A2 | 12/2006 |
| WO | 2008021419 A2 | 2/2008 |

OTHER PUBLICATIONS

Inscoe, Losses due to Adsorption during Filtration of Aqueous Solutions of Polycyclic Aromatic Hydrocarbons. Nature, 211, 1083-1085, 1966.*
Shi et al., DNA Extraction from Archival Formalin-fixed, Paraffin-embedded Tissue Sections Based on the Antigen Retrieval Principle: Heating Under the Influence of pH.The Journal of Histochemistry & Cytochemistry, 50, 1005-1011, 2002.*

* cited by examiner

Primary Examiner — Frank W Lu
(74) Attorney, Agent, or Firm — Rankin, Hill & Clark LLP

(57) ABSTRACT

The present invention relates to a method for recovering an aqueous phase comprising biomolecules dissolved therein from a multiphasic mixture, comprising at least said aqueous phase and a further liquid phase which is immiscible with said aqueous phase wherein said further liquid phase comprises at least one hydrocarbon compound. The invention further relates to the use of a hydrophilic filtering material, a device comprising such a filtering material or a kit comprising said device for recovering an aqueous phase comprising biomolecules dissolved therein from a mixture of said aqueous phase and at least one hydrocarbon compound comprising further liquid phase which is immiscible with said aqueous phase.

17 Claims, 7 Drawing Sheets
Specification includes a Sequence Listing.

SEQUENCE LISTING

```
<160> NUMBER OF SEQ ID NOS: 1

<210> SEQ ID NO 1
<211> LENGTH: 17
<212> TYPE: DNA
<213> ORGANISM: Homo sapiens

<400> SEQUENCE: 1
tacgactcag atcgtag                                                    17
```

RECOVERY OF A BIOMOLECULE COMPRISING AQUEOUS PHASE FROM A MULTIPHASIC MIXTURE

The present invention relates to a method for recovering an aqueous phase comprising biomolecules dissolved therein from a multiphasic mixture, comprising at least said aqueous phase and a further liquid phase which is immiscible with said aqueous phase wherein said further liquid phase comprises at least one hydrocarbon compound. The invention further relates to the use of a hydrophilic filtering material, a device comprising such a filtering material or a kit comprising said device for recovering an aqueous phase comprising biomolecules dissolved therein from a mixture of said aqueous phase and at least one hydrocarbon compound comprising further liquid phase which is immiscible with said aqueous phase.

For long-time storage and/or histological examination biological specimens are commonly preserved by inducing cross-linking of proteins within the sample by a chemical fixative such as for example formalin, thus preserving both, tissue structure and cellular morphology. After fixation, the samples are usually embedded in a wax, most commonly paraffin, in order to permit sectioning and mounting of the specimens for microscopic and/or histochemical applications.

In recent years, methods for isolating and analysing macromolecules, including DNA, RNA and only very recently even proteins from such wax-embedded samples have been developed. These applications, however, usually require the removal of the embedding medium from the sample (so-called "dewaxing"/"deparaffinisation") prior to any further process steps. As well, dewaxing is also advantageous in many histological staining protocols.

Traditionally dewaxing involves the use of aromatic solvents such as toluene and, in particular, xylene. Typically, a fresh slice or a microscope slide-mounted specimen is immersed in a xylene bath until the paraffin is solubilised. In subsequent steps the deparaffinised specimen is washed by a series of alcohol solutions of decreasing alcohol concentration to remove xylene, prior to a final wash using water, in order to make the sample accessible for aqueous reactant/reagent solutions, such as for example lysis buffers or staining solutions. Xylene, however, is a flammable, volatile and toxic organic solvent. For this reason, considerable efforts have been made during the past years to replace xylene with less toxic deparaffinisation agents. Examples for xylene replacements in histochemical applications include mineral and terpene oils, such as d-limonene, and aliphatic or isoparaffinic hydrocarbons (R. J. Buesa, M. V. Peshov, *Annals of Diagnostic Pathology* 2009, 13, 246-256).

In the co-pending European patent application no. 10 165 799.7 of the same applicant a method of extracting biomolecules from wax-embedded samples is described, wherein lysis of the sample cells in order to release the biomolecules into solution for further steps of detecting, analysing, isolating and/or purifying them is accomplished in a bi- or multi-phasic system, comprising at least an aqueous lysis buffer and an organic phase comprising a wax-solubilising agent and the solubilised wax.

Another approach is to simply suspend the embedded biological sample in an aqueous solution, then incubating it at a temperature above the melting point of the embedding medium to release cell material into solution for further processing (see for example WO 02/46463 A2).

Both of the aforementioned methods avoid the use of toxic deparaffinisation agents and laborious washing steps, however, a step of physically removing the dissolved, molten or re-solidified embedding medium from the aqueous phase, comprising the biomolecules dissolved therein, still is necessary. The step of recovering the aqueous phase, comprising biomolecules dissolved therein, from the bi- or multi-phasic mixture, formed from said aqueous phase and the hydrocarbon-comprising phase usually is carried out by decanting the hydrophobic layer of the top, aspirating either of the layers from the other or pipetting the layers from each other. However, all of the aforementioned methods for recovering one layer from the other cannot be automated or are at least trouble-prone if automated.

Commonly, filtration is used for separating solid materials from fluids, and conventional filtration units, such as a frit, a sieve etc. usually are not suitable for separating a mixture of immiscible liquids.

In the field of decontaminating water, so-called cross-flow filtration (also known as tangential flow filtration) is used for separating liquid mixtures of water and hydrocarbons, e.g. oils (see for example U.S. Pat. No. 5,158,681 and DE 43 00 438 C1). In cross-flow filtration the feed is directed tangentially along the filter surface (usually a membrane) at positive pressure, whereby a portion of the material is able to pass the membrane by permeating through its pores. In conventional so-called dead-end filtration the feed is directed onto the filter surface, the filtrate is passing the filter and leaving it at the opposed end, while the retentate is trapped in the filter and/or on its surface. While cross-flow filtration allows continuous processing, it is less suitable for rapid low-cost processing of a plurality of small sample volumes, in particular in view of automation.

Accordingly, the problem of the present invention was to provide a method for recovering an aqueous phase, comprising biomolecules of interest dissolved therein, from a multi-phasic mixture, comprising said aqueous phase and at least a further liquid phase immiscible with said aqueous phase wherein said further liquid phase comprises at least one hydrocarbon compound, wherein said method can be used during a fully automated method for isolation of said biomolecules.

This object is met by the method of the present invention. It has surprisingly been found that an aqueous phase, comprising biomolecules of interest dissolved therein, can be recovered in a fast and reliable manner from a multi-phasic mixture, comprising at least said aqueous phase and a further liquid phase, which is immiscible with said aqueous phase and comprises at least one hydrocarbon compound, by directing a feed of the multi-phasic mixture onto the surface of a filtering unit which is permeable for the aqueous phase including any biomolecules of interest dissolved therein, but impermeable for the further liquid phase comprising the at least one hydrocarbon compound.

Thus, the present invention provides a method for recovering an aqueous phase, comprising biomolecules of interest dissolved therein, from a multiphasic mixture, comprising at least said aqueous phase and a further liquid phase which is immiscible with said aqueous phase and comprises at least one hydrocarbon compound, said method comprising a step of directing a feed of the multiphasic mixture onto the surface of a filtering unit which is permeable for the aqueous phase including any biomolecules of interest dissolved therein, but impermeable for the further liquid phase comprising the at least one hydrocarbon compound. In particular the inventive method can be used in a method for isolating the biomolecules of interest from said multiphasic mixture.

In comparison to the methods known from the state of the art for this purpose, the method of the present invention allows a fast and reliable separation of an aqueous phase comprising biomolecules of interest dissolved therein from a further liquid phase, the latter e.g. comprising liquefied embedding medium, like liquefied paraffin from an FFPE sample, which can be fully automated. As well, the method of the present invention may be used for separating other hydrophobic compounds, e.g. fats or oils, from a biological sample with the aid of one or more alkyl solvents avoiding the usual time-consuming liquid-liquid extraction steps.

In terms of the present invention the term "recovering the aqueous phase from the multiphasic mixture" means a physical (spatial) separation of one phase from the other, and not only the collapsing of, for example, an emulsion. The term "multiphasic mixture" includes mixtures comprising 2, 3, 4 etc. phases, under the proviso that the mixture comprises at least one aqueous phase comprising biomolecules dissolved therein, and a further liquid phase which is immiscible with said aqueous phase wherein said further liquid phase comprises at least one hydrocarbon compound. However, the multiphasic mixture may as well comprise more than two different phases, for example a third phase representing a solid which is insoluble in both, the aqueous as well as the further liquid phase comprising the at least one hydrocarbon compound, a stable emulsion phase or any interphase(s). In most cases and preferably, the multiphasic mixture of the present invention however may represent a liquid biphasic mixture, comprising exactly the one aqueous phase and the one further liquid phase which comprises the at least one hydrocarbon compound (independent from any interphase).

In terms of the present invention the further liquid phase is immiscible with water if it does not form a homogenous solution with water upon mixing at room temperature (23° C.+/−2° C.). In terms of the present invention the term "at least one hydrocarbon compound" refers to any organic compound comprising, preferably consisting of carbon and hydrogen, including linear and branched aliphatic and cyclic hydrocarbons, including aromatic hydrocarbons such as for example xylene or toluene. Preferably, the at least one hydrocarbon compound of the present invention is selected from the group comprising linear and cyclic alkanes, olefins, the latter comprising hydrocarbons with 1, 2, 3 or more C=C double bonds, including terpentenes such as limonene, arenes, preferably substituted or unsubstituted mono- and/or bicyclic homocyclic arenes, such as for example xylene or toluene, and/or all kinds of substituted or unsubstituted mono-, bi- and/or polycyclic heterocyclic arenes and mixtures thereof. Preferably said hydrocarbon compound(s) may have a boiling point above room temperature (23° C.+/−2° C.) under atmospheric pressure (1,013.25 mbar).

In terms of the present invention, the hydrocarbon compound present in the further liquid phase preferably may represent (1) an alkyl solvent or a mixture of alkyl solvents, such as for example tetradecane, hexadecane or mineral oil, (2) molten paraffin or paraffin dissolved in an organic solvent, which is immiscible with the aqueous phase, but does not represent an alkyl solvent. More preferably, the liquid phase may comprise (3) both, an alkyl solvent (1) and paraffin dissolved therein (2), thus comprising a mixture of hydrocarbon compounds.

Preferably, the at least one hydrocarbon compound (or each of the hydrocarbon compounds, if a mixture of hydrocarbon compounds is present in the further liquid phase) has a chain length of at least six carbon atoms, more preferably of at least ten, even more preferably of at least fourteen and most preferably of at least sixteen carbon atoms, corresponding to for example the linear unbranched alkanes hexane, decane, tetradecane and hexadecane, respectively, as alkyl solvents. The further liquid phase is immiscible with the aqueous phase comprising dissolved biomolecules of interest and comprises preferably a mixture of different hydrocarbon compounds, preferably a mixture of hydrocarbon compounds of different chain length, such as for example paraffin, being a mixture of primarily saturated hydrocarbons solid at room temperature, which is typically prepared by distillation of petroleum. Said further liquid phase may comprise additional hydrocarbon compounds, such as for example linear alkyl solvents (linear alkanes liquid at room temperature), e.g. it may represent a mixture of paraffin and an organic solvent, e.g. hexadecane or a solution of paraffin in a hydrocarbon solvent like hexadecane, mineral oil, d-limonene etc. Even though said further liquid phase may comprise additional components which do not represent a hydrocarbon compound, but for example an ester, an aldehyde, or the like, the amount of hydrocarbon compounds in said phase preferably may be above 50%, more preferably above 75%, even more preferably above 90% and most preferably above 95% (w/w).

Physical separation of the aqueous phase, comprising the biomolecules, from the further liquid phase immiscible with said aqueous phase is achieved by directing a feed of the multi-phasic mixture onto the surface of a filtering unit. In terms of the present invention a filtering unit comprises at least one hydrophilic filtering material, which preferably may be supported by a sustaining structure. Alternatively or in addition, the filtering unit may comprise a prefiltration structure. Thus, herein the term "filtering unit" covers (i) the hydrophilic filtering material in combination with (ii) the prefiltration and (iii) the sustaining structure, if one or both of the latter (ii and iii) are present. The hydrophilic filtering material comprised in the filtering unit allows the aqueous phase to pass, but retains the further liquid phase. Thus, in contrast to the cross-flow membrane separation techniques known in the state of the art for separating mixtures of oil and water, the feed does not pass the membrane in a tangential manner, but is directed onto the filtering material, e.g. a membrane, with an impact angle of from 15 to 165°, preferably of from 30 to 150°, more preferably of from 45 to 135°, even more preferably of from 70 to 110° and most preferably in an essentially perpendicular manner (impact angle of 90°+/−5°).

The difference is illustrated in FIGS. 1 and 2: In cross-flow filtration (FIG. 1) the feed (1) passes tangentially across the filter/membrane surface (3), whereupon a fraction of the flow permeates the membrane and is separated from the flow in an angle of about 90° (filtrate/permate 4), while the retentate (2) is transported along the membrane with the flow (1).

In the method of the present invention (FIG. 2), the feed (1) is directed onto the filter/membrane surface (3), the filtrate (4) is passing the filter/membrane (3), while the retentate (2) is trapped at the opposed side of the filter.

In the method of the present invention it is assumed that the separation of the aqueous and the further liquid phase relies (mostly) on a physical separation by filtration. Based thereon, the method of the present invention also clearly is advantageous in comparison to separation methods based on adsorption processes. For instance, in adsorption-based methods the adsorbing structure, e.g. a membrane, always has to be selected in light of the specific chemical structure of the compounds to be removed to allow adsorbing/binding interaction between the adsorbing/binding structure and the compound. Furthermore, the amount of compound which can be removed from a sample usually is limited by the number of interacting/binding sites in the adsorbing/binding structure. In contrast, the method of the present invention can be applied to a large variety of different chemical compounds without the need for specifically adapting the filtering unit. Further, very large quantities of compounds may be removed from a sample using rather small filtering units, since the method of the present invention is not limited by a number of possible interacting/binding sites in the filtering units. Thus, the method of the present invention may also be applied, if the ratio of the number of molecules to be separated from the aqueous phase to the number of all sites in the filtering unit, which possibly could bind/interact with said molecules by electrostatic, ionic and/or van der Waals interactions or covalent binding, is >1, >10, >50 or even >100.

In terms of the present invention a filtering unit comprises at least one hydrophilic filtering material, which preferably may be supported by a sustaining structure. Alternatively or in addition, the filtering unit may comprise a prefiltration structure.

Thus, herein the term "filtering unit" covers (i) the hydrophilic filtering material in combination with (ii) the prefiltration and (iii) the sustaining structure, if one or both of the latter (ii and iii) are present. The hydrophilic filtering material comprised in the filtering unit allows the aqueous phase to pass, but retains the further liquid phase.

The hydrophilic filtering material used in the present invention is permeable for the aqueous phase, including any biomolecules of interest dissolved therein, but is impermeable for the further liquid phase comprising the at least one hydrocarbon compound. In terms of the present invention "permeable for the aqueous phase including any biomolecules of interest dissolved therein" means that any biomolecules to be detected, analysed, isolated and/or purified during further processing of the sample is essentially not repelled, retained, absorbed, bound or the like by/to any part of the filtering unit during the step of passing the aqueous phase through said filtering unit. Preferably less than 0.1 µg of the biomolecules of interest are retained per mg membrane. In terms of the present invention a filtering material is impermeable for the further liquid phase if less than 10 µL, preferably less than 5 µL, more preferably less than 1 µL and most preferably less than 0.1 µL of 100 µL of said further liquid phase passes the filtering material when spun in a centrifuge at 1,000×g, preferably at 2,000×g, more preferably at 3,500×g, even more preferably at 5,000×g and most preferably at 6,000×g for 1 minute.

Preferably, the filtering unit comprises at least one hydrophilic filtering material, preferably in the form of a membrane, a filter, a frit with a small pore diameter (e.g. of about 0.2 µm), a film, a fleece, a porous monolithic block, or a filtering bed comprising powder, particles, beads, granules, or spheres of a hydrophilic filtering material. Preferably, the hydrophilic filtering material is not present in the form of hollow fibres.

Preferably, the hydrophilic filtering material may be selected from the group comprising cellulose acetate (CA), polyamide (PA), polyethersulfone (PES) and polyvinylidene fluoride (PVDF) or mixtures thereof, e.g. mixtures of CA and PA; CA and PES; CA and PVDF; CA, PA and PES; CA, PA and PVDF; CA, PA, PES and PVDF; PA and PES; PA and PVDF, PA, PES and PVDF or PES and PVDF. More preferably, the hydrophilic filtering material is selected from the group comprising cellulose acetate and polyamide. Preferably the filtering material has a maximum pore size of 0.45 µm, more preferably of 0.40 µm, even more preferably of 0.35, 0.30, 0.29 or 0.25 µm and most preferably of 0.22 µm.

The minimum pore size may preferably be at least 0.01 µm, more preferably at least 0.05 µm, even more preferably at least 0.10 or 0.15 µm and most preferably at least 0.20 µm.

The thickness of the hydrophilic filtering material preferably may be at least 10 µm, more preferably at least 25 µm, even more preferably at least 50 µm, particularly preferably at least 75 µm and most preferably at least 100 µm.

The hydrophilic filtering material preferably may have a flow rate for water per $cm^2$ of about 5 to 50 mL/min, more preferably of about 10 to 30 mL/min, determined at a pressure difference of 1 bar according to DIN 58355.

The hydrophilic filtering material preferably may have a bubble point with water of about at least 2.0 bar, more preferably of at least 2.5 bar and even more preferably of at least 2.9 bar, determined at room temperature according to DIN 58355.

In addition to at least one layer of hydrophilic filtering material, the filtering unit of the present invention may comprise a prefiltration structure permeable for both, the aqueous and the further liquid phase in order to prevent solid particles from clogging the surface of the hydrophilic filtering material and/or a sustaining structure, supporting the hydrophilic filtering material and holding it in place. Both, the prefiltration structure and the sustaining structure may be independently present in the form of a frit, a sieve plate or the like, without being limited to these, and may be made of any inert material interfering neither with the hydrocarbon compound, nor the aqueous phase nor any biomolecules dissolved therein, such as for example polyethylene.

In the method of the present invention, the aqueous phase may preferably pass through the filtering unit by gravity, pressure, vacuum, suction, or centrifugation. In order to accelerate the separation process, the aqueous phase may preferably be forced through the filtering unit by applying pressure, vacuum/suction or centrifugal forces, without being limited to them. The force/power preferably applied to the filtering unit depends upon the phases to be separated and the filtering material used. Appropriate ranges of said forces, which allow separation at a reasonable speed without damaging the filtering unit and/or making it permeable for the further liquid phase, can easily be determined by routine experiments.

As said above the multiphasic mixture preferably is a biphasic mixture containing the aqueous phase and the further liquid phase which is immiscible with the aqueous phase. Said further liquid phase preferably may comprise a mixture of hydrocarbon compounds as described above.

Preferably the multiphasic mixture directed onto the surface of the filtering unit does not represent an emulsion of the aqueous phase in said further liquid phase or vice versa (w/o- or o/w-emulsion, respectively). Preferably the aqueous phase and said further liquid phase are present in the form of two essentially separated liquid phases although being in physical contact with one another. Preferably, the aqueous and the further liquid phase do not have the same density, so that the mixture of the two phases preferably is present in the form of two separate layers, being in physical contact with each other at the liquid-liquid interphase. Preferably, the density of the further liquid phase may be lower than the density of the aqueous phase, more preferably the density of the further liquid phase is below 1 g/mL. Preferably, more than 50%, more preferably more than 75%, even more preferably more than 90% and most preferably more than 95% (w/w) of the multiphasic mixture are not present in form of an emulsion when contacted with the surface of the filtering unit. If the multiphasic mixture is present as an emulsion, said emulsion may be spun in a centrifuge prior to being contacted with the filtering unit, in order to separate the emulsion into two separate layers, being in physical contact with each other at the liquid-liquid interphase.

The multiphasic mixture may be obtained by contacting a wax-embedded biological sample with at least an aqueous lysis buffer and optionally heating said sample in the presence of said aqueous lysis buffer.

Preferably, the multiphasic mixture may be obtained by:
1) contacting a wax-embedded biological sample with a wax-solubilising agent comprising at least one organic solvent immiscible with water;
2) optionally incubating the sample obtained in step 1;
3) adding an aqueous lysis buffer to the sample still comprising the wax-solubilising agent;
4) incubating the mixture obtained in step 3 to obtain the multiphasic mixture, comprising at least one organic phase as the at least one further liquid phase, said organic phase essentially comprising the dissolved wax and the wax-solubilising agent, and an aqueous phase, said aqueous phase comprising the dissolved biomolecules of interest, wherein steps 1 and 3 may as well be carried out as one combined step, if step 2 is omitted.

In terms of the present invention, the term "wax-embedded sample" comprises any biological sample embedded in a wax, for example prepared for histochemical or further chemical and/or biological analysis. Such a wax usually consists of a complex mixture of higher hydrocarbons and may include further components such as esters of higher fatty acids and/or glycols and the like. However, any other wax suitable to be used as an embedding medium for biological samples which is soluble in hydrocarbons, such as for example polyester wax, may be used as well. The wax may be of natural and/or synthetic origin and may additionally contain additives enhancing or improving its sample-embedding properties or particular characteristics of the wax, such as for example small amounts of organic polymers, DMSO or higher polyolefins. Preferably, the wax may represent paraffin, being a mixture of primarily saturated hydrocarbons solid at room temperature, which typically is prepared by distillation of petroleum. Independently of which type of paraffin is used, so-called high or low melting paraffin or a mixture thereof, the sample may be processed using the method, the device and/or the kit of the present invention.

Preferably, the sample may be a formalin-fixed paraffin-embedded sample, wherein the biological sample has been fixed using formaldehyde prior to being embedded in paraffin. The biological sample may be a whole organism, a part of an organism, in particular a tissue fragment or a tissue section, originating from humans, animals or plants, or microorganisms such as for example bacteria, yeast viruses or fungi. Embedded cells isolated from cell cultures may be used as well.

As a lysis buffer any aqueous solution may be used which is able to lyse/destroy the cells in a cell-containing material, thus releasing biomolecules comprised therein into solution without destroying the biomolecules of interest. Which type of lysis buffer is suitable to release the biomolecules of interest from the cells depends on the cell type and is known to skilled persons. Many aqueous lysis buffers are known from the state of the art which can be used in the method of the present invention. If the embedded sample is a fixed sample, for example a formalin fixed sample, said lysis buffer may contain additional components known in the state of the art for reducing the number of crosslinks in the sample. However, the presence of such additional components in the lysis buffer is not mandatory, as the crosslinks may be efficiently removed during incubation according to step 4 of the embodiment described above, even in the absence of compounds for reducing the number of crosslinks, e.g. if an incubation temperature of about 90° C. is applied.

A great advantage of this embodiment of the method of the present invention is the fact that no toxic chemicals are needed for dewaxing the sample. Furthermore no laborious washing steps or specifically adapted resins are necessary to separate the dissolved wax from the sample. In addition, the lysis buffer used in step 3 as well as any further reagents and means used in the optional step of isolating and/or purifying the nucleic acids from the aqueous phase after collecting the recovered aqueous phase may be almost freely selectable from a wide range of methods and/or means. This means that the method can be specifically adapted to a sample's particular requirements.

The wax-solubilizing agent preferably may be non-toxic and may comprise at least one organic solvent/compound immiscible with water. The wax-solubilizing agent may be liquid, at least for the moment of contacting it with the wax comprising sample. Preferably said solvent may represent a hydrocarbon compound, preferably selected from the group comprising linear, branched and cyclic $C_6$-$C_{16}$ alkanes or mixtures thereof, more preferably selected from the group comprising $C_{10}$-$C_{16}$ alkanes or mixtures thereof, even more preferably selected from the group comprising $C_{13}$-$C_{16}$ alkanes, or mixtures thereof, and most preferably it may represent tetradecane, pentadecane or hexadecane. Aromatic solvents such as, for example, xylene, toluene or mixtures thereof may be used as well. The melting point of any solvent applied to the wax-embedded sample for dewaxing, either in a pure form or as a mixture of solvents, respectively, preferably is below room temperature (23±2° C.) at atmospheric pressure. Furthermore, said solvent or mixture of solvents should neither be soluble in water, i.e. it should have a solubility in water of less than 0.01% (w/w), nor should it be miscible with water, i.e. it should not form an homogeneous solution with water upon mixing. Herein, the term "pure form" refers to a solvent applied to the wax-embedded sample in order to dissolve the wax without being diluted previously and/or mixed with other solvents. It does however not refer to a particular purity grade with respect to the presence of further compounds which do not represent a solvent. If a solvent is applied to the sample in a pure form it preferably has a melting point below room temperature. "Solvents" having a melting point above room temperature, however may be applied to the wax-embedded sample, if they are present in a mixture of solvents, which is liquid at room temperature (23±2° C.) at atmospheric pressure.

Preferably, the solvent or the mixture of solvents has/have a boiling point above 150° C., more preferably above 200° C. and most preferably above 250° C. at atmospheric pressure. Choosing a wax-solubilizing agent having a boiling point above 150° C. ensures that the sample's paraffin once liquefied stays in the liquid state and does not resolidify due to an unintended evaporation of the wax-solubilizing agent. In addition, it has been found that the above mentioned organic solvents or mixtures thereof in general have a very low tendency for forming stable emulsions with the aqueous phase obtained after adding the lysis buffer according to step 3. This is surprisingly true even in the presence of detergents like SDS. In addition, the above solvents are able to dissolve the solid paraffins within a few seconds or at most a few minutes (preferably of from about 15 seconds to about 15 minutes) at room temperature.

A dye/a colorant may be added to or comprised in the wax-solubilizing agent which is soluble in said wax-solubilizing agent, but insoluble in water, such as for instance anthraquinone solvent dyes being insoluble in water, e.g. 1,4-bis[(4-methylphenyl)amino]-9,10-anthracenedione, commercially available as "oil green". For example, an amount as small as about 1 µg of "oil green" in about 30 mL of the wax-solubilizing agent, e.g. hexadecane, equalling approximately 0.003% (w/v), is enough to impart an intense colour to the organic phase, while the colour of the aqueous phase remains unchanged, which significantly facilitates visual control of complete phase separation and recovery of the aqueous phase.

The step of incubating the mixture of the wax-solubilizing agent in the wax-embedded sample according to step 2 may be carried out at a temperature in the range of from 15 to 85° C., preferably of from 20 to 55° C., more preferably of from room temperature to 35° C. and most preferably at room temperature. If this incubation step is carried out, it may preferably last from 1 second to 3 hours, more preferably from 10 seconds to 1 hour, even more preferably from 20 seconds to 30 minutes and most preferably from 30 seconds to 5 minutes. As well, the wax-solubilizing agent and the aqueous lysis buffer may be applied to the sample simultaneously or "almost simultaneously", i.e. one immediately after the other, that is the dewaxing agent immediately after the lysis buffer or vice versa. In this case, optional step 2 is omitted and steps 1 and 3 are carried out simultaneously or "almost simultaneously".

In a preferred embodiment of the method of the present invention which makes use of the above-mentioned alkanes as wax-solubilising agents it is particularly advantageous that the embedding medium can be recovered from the sample very quickly and in an (almost) quantitative manner at low temperatures, even if an aqueous lysis buffer is added to the sample simultaneously with the wax-solubilizing agent or "almost simultaneously". In consequence, there is no need for laborious and time-consuming dewaxing and phase separating steps prior to cell lysis.

Thus, in contrast to several methods known from the state of the art no elevated temperatures and/or long incubation times are needed for removing the wax which may have a negative impact on the quality and yield of the biomolecules, e.g. the nucleic acids, in particular if nucleic acid-digesting enzymes are present in the sample, such as RNases and DNases, which have not (yet) been inactivated by a proteinase. The removal of paraffin prior to or simultaneously with the lysis shortens the required lysis time, as the aqueous lysis buffer can penetrate a deparaffinised sample more quickly and efficiently than an embedded one, i.e. a shorter lysis time and/or a lower lysis temperature may be applied. Recovery of the biomolecule-comprising aqueous phase is then be achieved by the method of the present invention in a fast and reliable manner, so that the whole method including lysis and separation is fast and can be automated.

As said above it is even not necessary to incubate the sample in contact with the wax-solubilizing agent prior to the addition of an aqueous lysis buffer. As well the wax-solubilizing agent and the aqueous lysis buffer may be added to the sample simultaneously. In this case, the sample preferably is mixed to ensure a thorough contacting of the phases, for example by vortexing, shaking on a laboratory shaker, pipetting up and down etc., without being limited to these. Additional compounds, such as a protease, may be added as well.

A further advantage is the universal application of the method of the present invention in combination with a wide range of lysis buffer and lysis protocols known from the state of the art, such as for example buffer ATL comprised in the QIAamp FFPE kit, buffer P1 comprised in the QIAsymphony DNA kit (both available from QIAGEN, Hilden, Germany), or buffer PBS. The lysis buffer may for example comprise a buffering agent, preferably selected from the group comprising Tris, Mops, Mes, Hepes, borates, phosphates and carbonates and at least a detergent, preferably selected from the group comprising nonionic, anionic, cationic and zwitterionic detergents, or a mixture thereof. More preferred the detergents are selected from anionic or zwitterionic detergents. Even more preferably the lysis buffer may comprise anionic detergents, most preferably sodium dodecyl sulfate. Furthermore nonionic surfactants, such as substituted phenol or sugar polyethoxylates, commercially available for instance as Triton X-114 (Dow Chemical Co., Midland, Mich., USA), Triton X-100 (Dow Chemical Co., Midland, Mich., USA) or Tween 20 (Merck, Darmstadt, Germany) may be used, as well as cationic surfactants, such as quaternary ammonium surfactants, e.g. cetyltrimethylammonium bromide (CTAB), tetradecyltrimethylammonium bromide (TTAB) or octyltrimethylammonium bromide (OTAB).

The lysis buffer may comprise one or more additional substances, preferably selected from the group comprising chelating agents, reducing agents, inorganic salts, such as ammonium sulphate, pH-indicators and stabilisers such as sodium azide. Preferably the lysis buffer may have a pH in the range of from 4 to 11, preferably of from 7 to 10 and most preferably of from 8 to 9.

In addition to a lysis buffer a proteolytic agent may be added to the mixture in step 3. The proteolytic agent may already be comprised in the lysis buffer added to the sample in step 3, as well. Said proteolytic agent may preferably be selected from the group comprising proteases and non-enzymatic proteolytic compounds and more preferably may represent proteinase K, trypsin, chymotrypsin, papain, pepsin, pronase, endoproteinase Lys-C, bromocyane, recombinant *Bacillus* proteases, such as for example QIAGEN protease Lysozyme, or a mixture thereof.

The step of incubating the mixture obtained after adding the aqueous lysis buffer to the sample according to step 4 may preferably be carried out at a temperature in the range of from 15 to 95° C., preferably of from 20 to 70° C. and most preferably of from 37 to 65° C., including 56° C. This incubation may preferably be carried out for 30 seconds to 24 hours, more preferably for 45 seconds to 12 hours, even more preferably for 50 seconds to 5 hours and most preferably for 1 minute to 2 hours. However, both, temperature and time of incubation may vary with the kind, amount and age of the sample and the lysis buffer employed. This is well known to a person skilled in the art, and optimum lysis conditions, in particular in respect of incubation time and temperature, can be easily determined by a person skilled in the art by means of routine experiments. In some cases, it may also be preferred to carry out a "two-step incubation" procedure, first incubating the mixture at a temperature in the range of 37 to 65° C. for e.g. about 1 min to about 3 h, then optionally recovering the aqueous phase from the organic phase according to the present invention and incubating the aqueous phase at an increased temperature e.g. up to about 90° C. for e.g. about 10 min to about 5 h. As well, optionally the recovery of the aqueous phase from the organic phase may be carried out after the incubation at an increased temperature like e.g. at 90° C. In this case the extent of unintended evaporation of the aqueous phase is decreased.

The method of the present invention may comprise a further step of collecting the aqueous phase after passing the filtering unit. Means and devices for collecting sample solution after passing the filtering unit are well known in the state of the art. The method, furthermore, may comprise any step of detecting, analysing, isolating and/or purifying biomolecules of interest from said aqueous phase, wherein the methods, devices and reagents depending upon the biomolecule to be detected, analysed, isolated and/or purified, are well known to a person skilled in the art.

In terms of the present invention "biomolecule" includes any nucleic acid like DNA or RNA, in particular linear, branched or circular, single stranded or double stranded nucleic acids, more particular mRNA, sRNA, miRNA, snRAN, tRNA, hnRNA or ribozymes, genomic, plasmid or organelles DNA; any nucleotide, oligonucleotide or polynucleotide, including synthetic, modified or labelled oligo- or polynucleotides; PCR-primers, short DNA or RNA fragments for hybridization; PNAs (peptide nucleic acids); any protein, peptide or amino acid, including unlabelled or labelled antibodies, receptors, hormones, growth factors and modified proteins, nucleic acids, proteins and peptides of infectious origin; metabolites, any lipid; sugar (monomer, oligomer or polymer); proteoglucanes; any low molecular pathway product, signal molecule, receptor or enzyme activator or inhibitor; medicaments and metabolites of medicaments, without being limited to these.

Preferably, the biomolecules represent nucleic acids. The nucleic acids preferably may be selected from the group comprising ribonucleic acids (RNA) and desoxyribonucleic acids (DNA), including naturally occurring, recombinant and/or chemically or biotechnically engineered nucleic acids of eukaryotic, prokaryotic or viral origin, including gDNA, cDNA, mRNA, tRNA, rRNA, miRNA, sRNA, piRNA, snRNA, LNA (locked nucleic acids), PNA (peptide nucleic acids), or fragments thereof, without being limited to these. When employing a suitable lysis buffer, such as, for instance, buffer PKD, commercially available from QIAGEN (Hilden, Germany), even both, DNA and RNA, may be isolated from the same sample using the method of the present invention. Preferably the nucleic acids may represent DNA, more preferably DNA having a length of at least 100 bp.

The step of isolating and/or purifying the biomolecules dissolved in the aqueous phase may preferably be carried out by means of at least one chromatographic and/or solid-phase-based method, including normal and reversed-phase chromatography, gel-filtration chromatography, ion-exchange chomatography, triple-helix-affinity chromatography, chaotrope-mediated or chaotrope-free affinity binding (adsorption), including adsorption to silica or polystyrene matrices/surfaces mediated by binding agents. Preferably, the at least one chromatographic and/or solid-phase-based method may be selected from the group comprising gel-filtration chromatography, ion-exchange chomatography, reversed-phase chromatography and affinity binding. Alternatively or in addition, the biomolecules may as well be purified by selectively precipitating either the biomolecule of interest or the impurities/undesired further compounds present in the sample. If the biomolecules of interest represent nucleic acids, proteins may for example be precipitated by adding cationic surfactants such as CTAB (cetyltrimethylammonium bromide).

Several kits are commercially available for the detection, analysis, isolation and/or purification of biomolecules, many of which can be used for detecting, analysing, isolating and/or purifying the biomolecules present in the aqueous phase recovered from a multiphasic mixture according to the present invention. These include for example the QIAamp, AllPrep DNA/RNA and QIAsymphony tissue kits (all of them QIAGEN, Hilden, Germany) if nucleic acids are to be isolated and/or purified, without being limited to these.

The present invention furthermore relates to the use of a hydrophilic filtering material, a device comprising said filtering material or a kit comprising said device for recovering an aqueous phase comprising biomolecules, preferably nucleic acids or proteins, dissolved therein from a further liquid phase immiscible with said aqueous phase wherein said further liquid phase comprises at least one hydrocarbon compound, preferably a wax dissolved in at least one organic solvent as described above. The organic solvent preferably is selected from the group comprising linear, branched and cyclic $C_6$-$C_{16}$ alkanes, olefins, or mixtures thereof, said further liquid phase more preferably representing paraffin dissolved in tetradecane, pentadecane, hexadecane, or a mixture thereof.

The device for carrying out the method of the present invention comprises a hollow body having an inlet and an outlet, said hollow body comprising a hydrophilic filtering material, preferably supported by a sustaining structure preferably in the form of a frit or a sieve plate.

The hydrophilic filtering material may preferably be in the form of a membrane, a filter, a frit with a small pore diameter (e.g. of about 0.2 µm), a film, a fleece, a porous monolithic block, or a filtering bed comprising powder, particles, beads, granules, or spheres of a hydrophilic filtering material. Preferably, the hydrophilic filtering material is not present in the form of hollow fibres.

Preferably, the hydrophilic filtering material may be selected from the group comprising cellulose acetate (CA), polyamide (PA), polyethersulfone (PES) and polyvinylidene fluoride (PVDF) or mixtures thereof, e.g. mixtures of CA and PA; CA and PES; CA and PVDF; CA, PA and PES; CA, PA and PVDF; CA, PA, PES and PVDF; PA and PES; PA and PVDF, PA, PES and PVDF or PES and PVDF. More preferably, the hydrophilic filtering material is selected from the group comprising cellulose acetate and polyamide and mixtures thereof. Preferably the filtering material has a maximum pore size of 0.45 µm, more preferably of 0.40 µm, even more preferably of 0.35, 0.30, 0.29 or 0.25 µm and most preferably of 0.22 µm. The minimum pore size may preferably be at least 0.01 µm, more preferably at least 0.05 µm, even more preferably at least 0.10 or 0.15 µm and most preferably at least 0.20 µm.

The thickness of the hydrophilic filtering material preferably may be at least 10 µm, more preferably at least 25 µm, even more preferably at least 50 µm, particularly preferably at least 75 µm and most preferably at least 100 µm.

The hydrophilic filtering material preferably may have a flow rate for water per $cm^2$ of about 5 to 50 mL/min, more preferably of about 10 to 30 mL/min, determined at a pressure difference of 1 bar according to DIN 58355.

The hydrophilic filtering material preferably may have a bubble point with water of about at least 2.0 bar, more preferably of at least 2.5 bar and even more preferably of at least 2.9 bar, determined at room temperature according to DIN 58355.

The hollow body may be made of any material suitable for sample collection, storage or treatment, like plastic, metal, glass, porcelain or the like. Preferably the body may be made of plastic, more preferably the body may be made of a thermoplastic resin like polypropylene, polyethylene, polypropylene-copolymers, polyvinylchloride, polyurethane, polycarbonate, polyamide, polyimide, polystyrene, polyethyleneterephthalate, polylactide, ethylene-polyvinylacetate, vinylchloride, vinylacetate copolymers, polyacetate, polyether alcohols, vinylacetate copolymers and the like without being limited to these.

Preferably the inlet of the device is an opening at the "upper end" of the device and the outlet is an opening at the "bottom side" of the device. Particularly preferably the inlet and the outlet are opposed to each other. Optionally the device may comprise at least one removable closing device to close the inlet and/or the outlet of the device. Inside the hollow body or at its bottom end, i.e. at the outlet side, the hollow body is equipped with at least one layer of the hydrophilic filtering material arranged in the flow area in such a way that essentially the whole aqueous phase present in the feed has to pass the layer of hydrophilic filtering material before leaving the hollow body through the outlet. Suitable hydrophilic filtering materials and their properties have been described above.

The device further may comprise preferably a sustaining structure supporting the layer of hydrophilic filtering material to improve its mechanical stability and to retain said material in place inside of the hollow body. Said sustaining structure may be e.g. in the form of a frit, a sieve plate or the like. The device furthermore may comprise a prefiltration structure placed above the hydrophilic filtering material to retain solid particles present in the feed which otherwise could clock the hydrophilic membrane. Said prefiltration structure may be in the form of a frit, a sieve plate, a filter, and the like. Preferably both, the prefiltration structure as well as the sustaining structure, neither interact with the compounds in particular the biomolecules of interest nor the solvents present in the multiphasic mixture which forms the feed by covalent or non-covalent binding, adsorption, chemical reaction, electrostatic or ionic interaction or the like. In terms of the present invention, a hydrophilic filtering unit combines at least one hydrophilic filtering material as described above with at least one of a prefiltration or a sustaining structure.

Preferably, the device may represent a funnel, a column body, a syringe, or a multi-well plate, more preferably a spin column, equipped with a hydrophilic filtering material or hydrophilic filtering unit as described above. Preferably, the device of the present invention represents a spin column equipped with such a hydrophilic filtering material/hydrophilic filtering unit.

The kit for carrying out the method of the present invention comprises a hydrophilic filtering material, preferably comprised in the device already described above and at least one additional component selected from the group comprising instructions for using the kit, a lysis buffer, a wax-solubilising agent, a proteolytic agent and a solid phase for purifying the biomolecule of interest by chromatography and/or affinity binding. The lysis buffer, the wax-solubilising agent and the proteolytic agent preferably may represent the ones described above.

FIGURES

Figure 6:
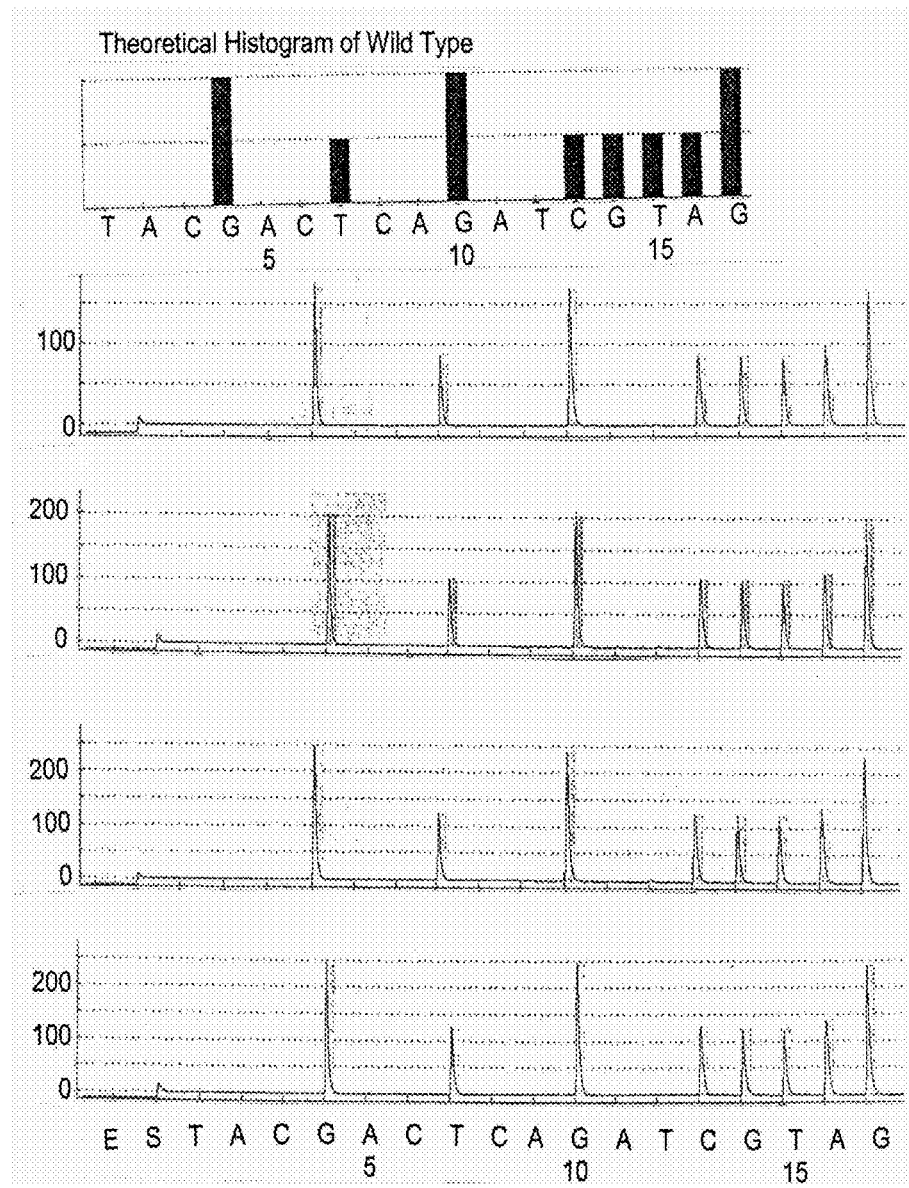

FIG. 6 shows the result of an analysis for mutations in codon 12 and 13 of KRAS in human tonsillar DNA obtained from a FFPE sample using the method of the present invention (example 2).

FIGS. 7a, 7b, 7c and 7d show different stages during the separation of an emulsion formed from an aqueous lysis buffer and a mixture of d-limonene and hexadecane using the method of the present invention (example 3).

Figure 8:
Figure 8:
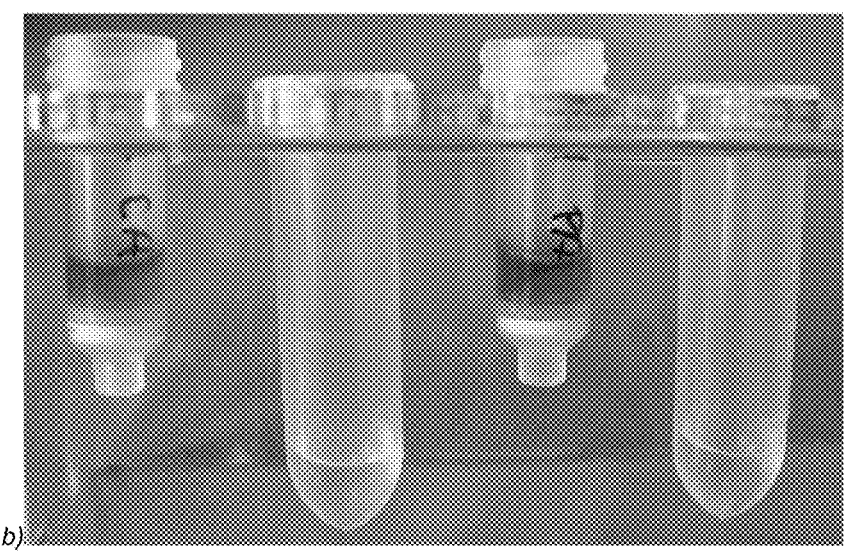

FIGS. 8a) and 8b) show different stages during the separation of an emulsion formed from an aqueous lysis buffer and xylene using the method of the present invention (example 4).

EXAMPLES

Example 1

Preparation of a Device According to the Present Invention

Into a standard spin column (QIAGEN, Hilden, Germany) equipped with a frit a cellulose acetate filter having a pore size of 0.2 µm (OE66, Schleicher & Schull Microscience GmbH, Dassel, Germany) was placed, cut to fit using a scalpel. To hold the filter in place during operation it was fixed with a plastic ring.

Example 2

Isolation of gDNA from FFPE Samples

Figure 1:
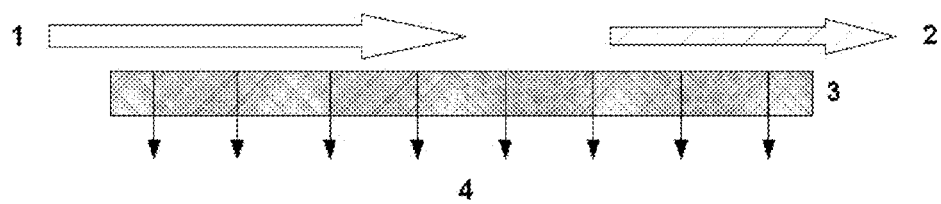
FIG. 1 illustrates the principle of cross-flow filtration.
Figure 2:
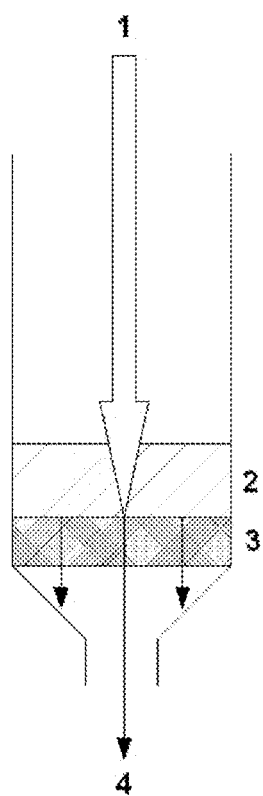
FIG. 2 illustrates the principle of dead-end filtration, the latter being used in the method of the present invention.
Figure 3:
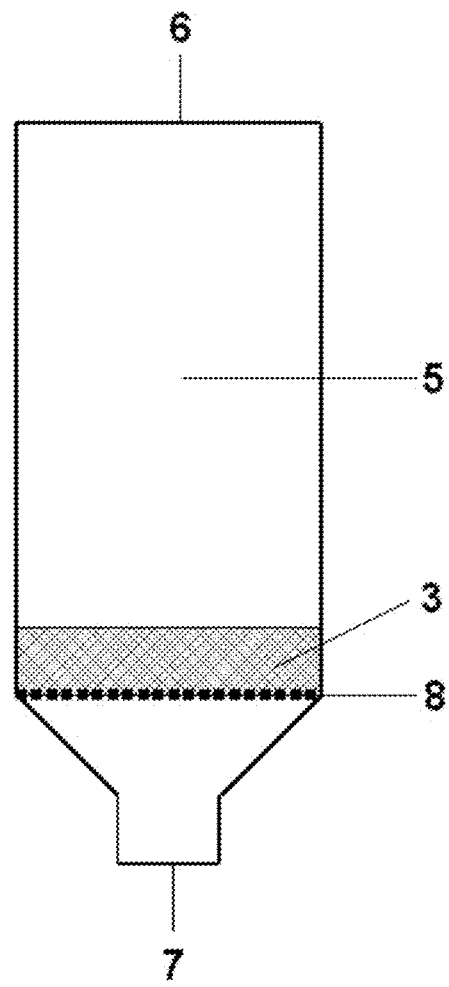
FIG. 3 shows one embodiment of the device of the present invention, which is a spin column comprising a hollow body (5), an inlet (6) and an outlet (7), said hollow body (5) equipped with a hydrophilic filtering material (3) supported by a sustaining structure (8) in the form of a porous frit.
Figure 4:
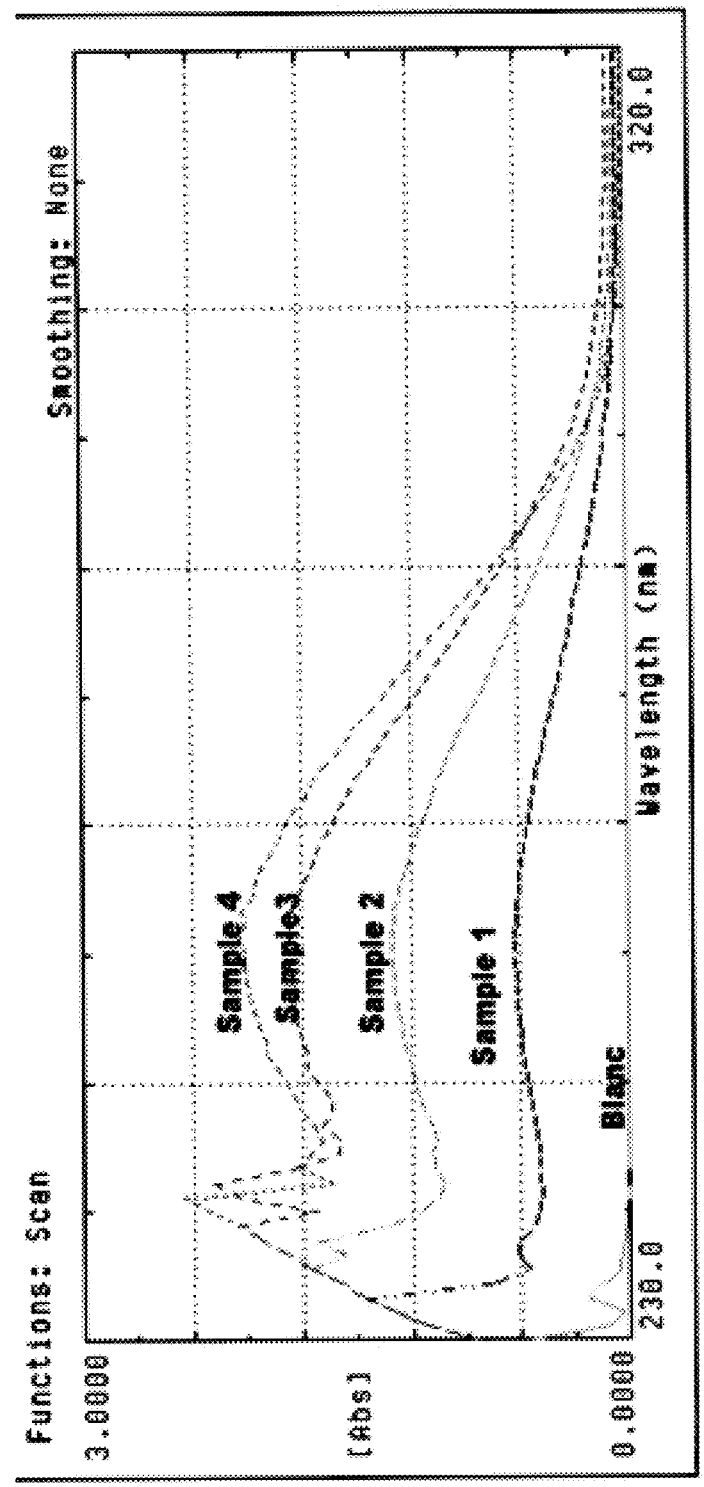
FIG. 4 shows an OD scan of four samples comprising gDNA, which have been isolated and purified from FFPE tissue sections according to the method of the present invention (see example 2).

Slices from FFPE blocks from rat liver (sample 1: one slice, sample 2: two slices, sample 3: three slices) and female human tonsil (sample 4: one slice) were placed in a reaction tube. Each slice had a thickness of 10 µm. 200 µL of the wax-solubilising agent described in copending application 10 165 799.7 comprising hexadecane and an oil-soluble dye, as well as 180 µL buffer ATL (QIAGEN, Hilden, Germany) as a lysis buffer and 20 µL proteinase K (QIAGEN, Hilden, Germany) were added to the sample. The sample was mixed by vortexing and shaken in a shaking incubator at 1,000 rpm for 1 hour at 56° C. The sample was centrifuged for 1 minute at 20,400×g at room temperature. To remove formaldehyde-induced crosslinks, the sample was then incubated for 1 hour at about 90° C. The upper hydrocarbon layer avoids evaporation of the aqueous phase during this step. The sample was allowed to cool to room temperature and transferred to the spin column of example 1. The sample was then centrifuged at 2,000×g, whereupon the aqueous phase passes the hydrophilic filtering unit, whereas the hydrocarbon phase, comprising the liquefied paraffin and the wax-solubilising agent, remains within the column. The aqueous phase was collected and purified according to the QIAamp FFPE Minelute Handbook using the columns provided in said kit. The samples were eluted from the Minelute columns using 100 µL buffer ATE (QIAGEN, Hilden, Germany) and diluted with further 100 µL of buffer ATE prior to optical density (OD) measurement in order to determine the amount of gDNA present in the sample. The results are presented in FIG. 4 showing the usual spectrum for gDNA samples diluted in buffer ATE. The amount of gDNA present in the samples is:

| | |
|---|---|
| sample 1 | 6.2 µg gDNA (one slice of 10 µm FFPE rat liver tissue) |
| sample 2 | 15.8 µg gDNA (two slices of 10 µm FFPE rat liver tissue) |
| sample 3 | 20.4 µg gDNA (three slices of 10 µm FFPE rat liver tissue) |
| sample 4 | 22.8 µg gDNA (one slice of 10 µm FFPE human tonsillar tissue) |

Figure 5:
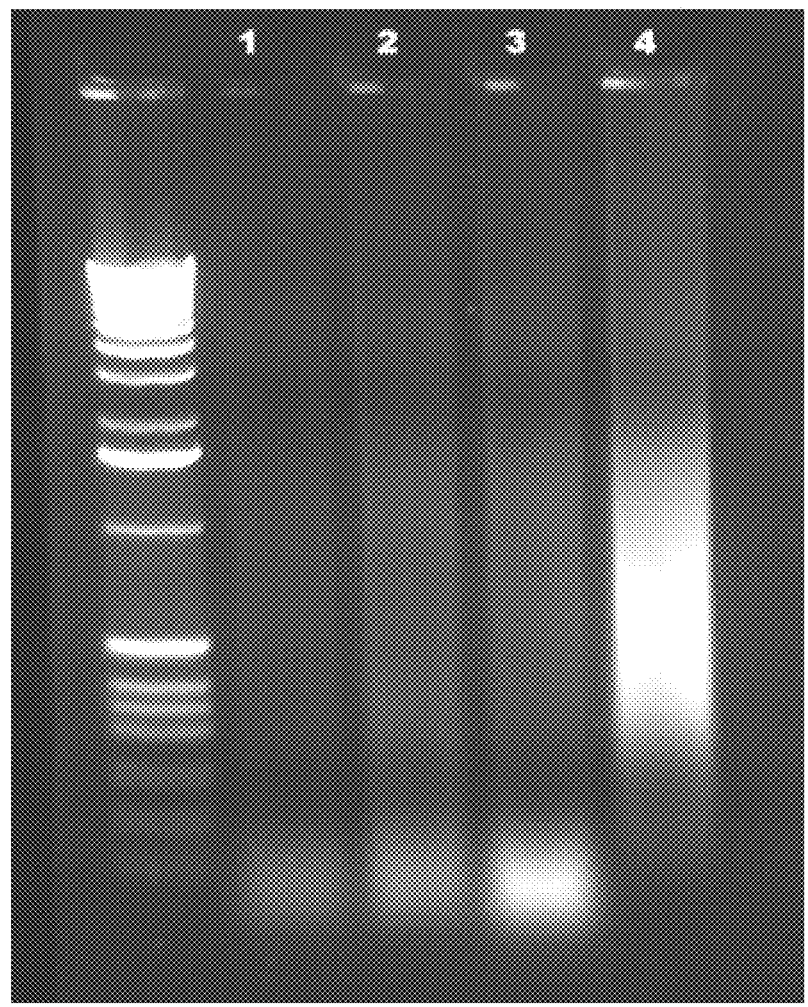
FIG. 5 shows the result of a gel-electrophoretic analysis of the above FFPE samples (example 2).

10 µL of each sample were analysed on an 0.8% agarose gel (50 mL) containing 2.5 µL Gel Red for 40 minutes at 100 V in 1×TAE buffer. As a blank buffer ATE was used. The result is presented in FIG. 5, showing a gel typical for gDNA isolated from FFPE samples.

As an example for a possible downstream analysis of the nucleic acids isolated from an FFPE sample using the method of the present invention, the gDNA obtained from sample 4 was screened for mutations in codons 12 and 13 of the KRAS gene by pyrosequencing using the commercially available Therascreen® KRAS Pyro® Kit (QIAGEN, Hilden, Germany) according to the manufacturer's protocol: Four samples, each containing 10 ng of gDNA from sample 4 were amplified in a PCR using primers targeting codons 12/13. The amplicons were immobilised on Streptavidin Sepharose® High Performance beads. Single-stranded DNA is prepared and pyrosequencing is carried out.

The results are presented in FIG. 6. All four examples show a typical histogram of a wild-type codon 12/13 of KRAS without mutation (for comparison the theoretical histogram of the wild type is shown as well). This further demonstrates that high-quality DNA can be obtained from FFPE samples using the method of the present invention, which can be used in downstream analyses without further purification.

Example 3

Figure 7:
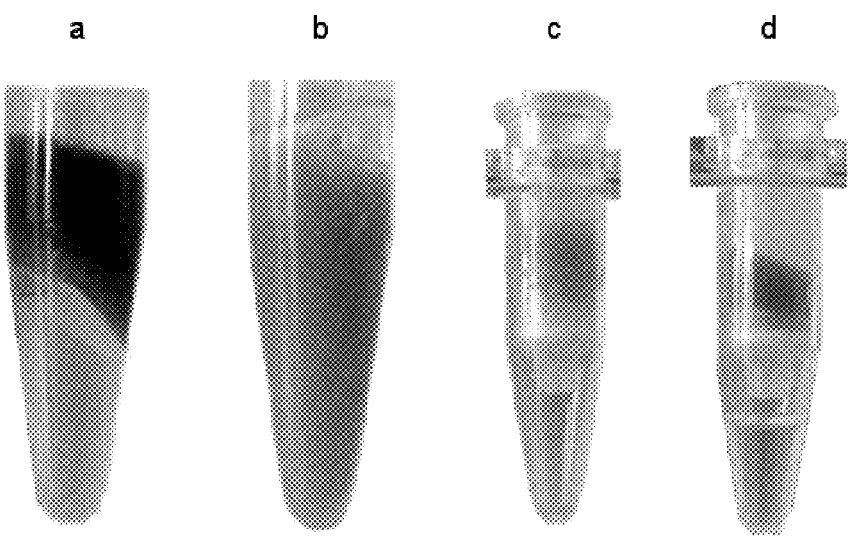

Recovery of an Aqueous Phase from a Mixture of Said Aqueous Phase and a d-Limonene Comprising Phase To 300 µL of an aqueous lysis buffer (50 mM Tris sulfate; 50 mM sodium dodecyl sulfate, pH 8.5) 200 µL of CitriSolv (Fisher Scientific, Schwerte, Germany) and 200 µL of hexadecane comprising oil green as a colorant were added. The biphasic mixture (FIG. 7a) was vortexed to form an emulsion (FIG. 7b). Said emulsion was transferred to the spin column of example 1 (FIG. 7c). The column was spun at 1,500×g for 2 minutes, whereupon the aqueous phase passes the hydrophilic filtering unit, whereas the hydrocarbon phase, comprising the d-limonene and hexadecane, remains within the column (FIG. 7d). This example shows that even emulsions of an aqueous phase and the further liquid phase may be separated by the method of the present invention.

Similar results were obtained using a hydrophilic polyamide filter (Sartolon Polyamid with a pore size of 0.2 µm from Sartorius, Göttingen, Germany).

Example 4

Recovery of an Aqueous Phase from a Mixture of Said Aqueous Phase and Xylene

For a better visibility, xylene was stained by adding a small amount of oil green prior to use. 200 µL xylene was mixed with an aqueous lysis buffer (50 mM Tris sulfate; 50 mM sodium dodecyl sulfate, pH 8.5). The mixture was vortexed until an emulsion had formed (FIG. 8a). Said emulsion was transferred onto a spin column equipped with a frit and one of the membranes already used in example 3, either made of cellulose acetate or polyamide. The column was then placed into a collection tube and spun in a bench-top centrifuge at 3,000×g for 1 minute. As can be seen from FIG. 8b in both cases the emulsion was broken and the aqueous phase was clearly separated from the organic phase. The results obtained using the cellulose acetate membrane are shown on the left hand side of FIG. 8b, while on the right hand side those obtained using a polyamide membrane are shown.

The invention claimed is:

1. A method for recovering an aqueous phase comprising biomolecules of interest from a multiphasic mixture comprising said aqueous phase and at least one organic phase which is immiscible with said aqueous phase, wherein the at least one organic phase comprises at least one organic solvent immiscible with water, said method comprising:
   1) contacting a wax-embedded biological sample comprising cells containing the biomolecules of interest with a wax-solubilising agent comprising the at least one organic solvent immiscible with water, thereby forming a first mixture comprising dissolved wax and the cells from the wax-embedded biological sample, and the wax-solubilising agent;
   2) optionally incubating the first mixture for a time period;
   3) adding an aqueous lysis buffer to the first mixture to release the biomolecules of interest from the cells, thereby forming a second mixture comprising the dissolved wax, the biomolecules of interest, the lysis buffer, and the wax-solubilising agent;
   4) incubating the second mixture for a time period, thereby obtaining the multiphasic mixture comprising the said aqueous phase and the at least one organic phase which is immiscible with said aqueous phase, said at least one organic phase comprising the dissolved wax and the wax-solubilising agent, and said aqueous phase comprising the biomolecules of interest;

5) directing a feed of the multiphasic mixture onto a surface of a filtering unit which is permeable for the aqueous phase but is impermeable for the at least one organic phase; and 6) recovering the aqueous phase from the multiphasic mixture by passing the aqueous phase through the filtering unit and collecting the aqueous phase.

2. The method according to claim 1, wherein the filtering unit comprises at least one hydrophilic filtering material.

3. The method according to claim 2, wherein the at least one hydrophilic filtering material is selected from the group comprising cellulose acetate, polyamide, polyethersulfone, polyvinylidene fluoride and mixtures thereof.

4. The method according to claim 2, wherein the at least one hydrophilic filtering material is in a form of a membrane, a filter, a frit, a film, a fleece, a porous monolithic block or a filtering bed comprising powder, particles, beads, granules, or spheres.

5. The method according to claim 1, wherein the aqueous phase is passed through the filtering unit based on gravity of the multiphasic mixture, by application of pressure, vacuum, or suction to the filtering unit, or by centrifugation of the filtering unit.

6. The method according to claim 1, wherein the multiphasic mixture is a biphasic mixture.

7. The method according to claim 1, wherein the wax-embedded biological sample is a paraffin-embedded biological sample.

8. The method according to claim 7, wherein the paraffin-embedded biological sample is a formalin-fixed paraffin-embedded biological sample.

9. The method according to claim 7, wherein the at least one organic solvent is a linear, branched or cyclic C6-C16 alkane, olefin, or mixture thereof.

10. The method according to claim 7, wherein the at least one organic solvent is a C13-C16 alkane or mixture thereof.

11. The method according to claim 7, wherein the at least one organic solvent is selected from the group consisting of tetradecane, pentadecane, and hexadecane.

12. The method according to claim 1, wherein a proteolytic agent is either added to the first mixture in step 3) or the lysis buffer comprises said proteolytic agent, said proteolytic agent being selected from the group comprising proteases and non-enzymatic proteolytic compounds.

13. The method according to claim 12, wherein said proteases and said non-enzymatic proteolytic compounds are selected from the group consisting of proteinase K, typsin, chymotrypsin, papain, pepsin, pronase, endoproteinase Lys-C, bromocyane, recombinant Bacillus proteases, Lysozyme, and mixtures thereof.

14. The method according to claim 1, further comprising a step of isolating and/or purifying the biomolecules from the aqueous phase.

15. The method according to claim 14 wherein said isolating and/or purifying biomolecules of interest from the aqueous phase are carried out by at least one of chromatographic method and solid-phase-based method selected from the group consisting of gel-filtration chromatography, ion-exchange chromatography, reversed-phase chromatography and affinity binding method.

16. The method according to claim 1, wherein steps 1) and 3) are carried out as one combined step such that only the second mixture is formed and the first mixture is not formed.

17. The method according to claim 1 wherein the biomolecules of interest are nucleic acids.

* * * * *

UNITED STATES PATENT AND TRADEMARK OFFICE
CERTIFICATE OF CORRECTION

PATENT NO. : 10,081,806 B2  
APPLICATION NO. : 14/357958  
DATED : September 25, 2018  
INVENTOR(S) : Jörg Hucklenbroich et al.

Page 1 of 1

It is certified that error appears in the above-identified patent and that said Letters Patent is hereby corrected as shown below:

In the Claims

In Column 17, Line 5,   delete "5directing a feed of the multiphasic mixture onto a surface"  
insert --5) directing a feed of the multiphasic mixture onto a surface--

In Column 17, Line 9,   delete "6recovering the aqueous phase from the multiphasic mix-"  
insert --6) recovering the aqueous phase from the multiphasic mix- --

Signed and Sealed this  
Fourth Day of December, 2018

Andrei Iancu  
*Director of the United States Patent and Trademark Office*